United States Patent [19]

Yamaguchi et al.

[11] Patent Number: 5,859,286
[45] Date of Patent: Jan. 12, 1999

[54] MONOMER, POLYMER OF THE SAME, AND COMPOSITION CONTAINING THE POLYMER

[75] Inventors: Shigeru Yamaguchi, Himeji; Keisi Tuboi, Akashi, both of Japan

[73] Assignee: Nippon Shokubai Co., Ltd., Osaka, Japan

[21] Appl. No.: 659,907

[22] Filed: Jun. 7, 1996

[30] Foreign Application Priority Data

Jun. 9, 1995 [JP] Japan .................................... 7-143740
Jun. 9, 1995 [JP] Japan .................................... 7-143742

[51] Int. Cl.[6] .................................................. C07C 69/52
[52] U.S. Cl. ............................................................ 560/205
[58] Field of Search ..................................... 560/181, 205

[56] References Cited

U.S. PATENT DOCUMENTS 5,064,563  11/1991  Yamaguchi et al. ............... 252/174.23

FOREIGN PATENT DOCUMENTS

| | | |
|---|---|---|
| 0 337 694 A2 | 10/1989 | European Pat. Off. . |
| 0 396 303 A2 | 11/1990 | European Pat. Off. . |
| 0 433 010 A2 | 6/1991 | European Pat. Off. . |
| 0433010 | 6/1991 | European Pat. Off. . |
| 0 435 505 A2 | 7/1991 | European Pat. Off. . |
| 0 529 910 B1 | 3/1993 | European Pat. Off. . |
| 0 668 298 A1 | 8/1995 | European Pat. Off. . |
| 7295221 | 11/1995 | Japan . |
| 1 438 066 | 6/1976 | United Kingdom . |
| 1438066 | 6/1976 | United Kingdom . |

OTHER PUBLICATIONS

Printout from the Registry of STN/CAS about the structured formulas of cis–and trans–coumaroyl–tartaric acid.
Chieko Yoneyama and Tadae Kushida, Yamanashi Daigaku Hakko Kenkyusho Kenkyu Hokoku, 15, 9–13, 1980.
Rosa M. Lamuela–Raventos and Andrew L. Waterhouse, American Journal of Enology and Viticulture 45(1), 1–5, 1994.

*Primary Examiner*—Jeffrey Smith
*Assistant Examiner*—Wu C. Cheng
*Attorney, Agent, or Firm*—Kubovcik & Kubovcik

[57] ABSTRACT

A monomer having a structure expressed as:

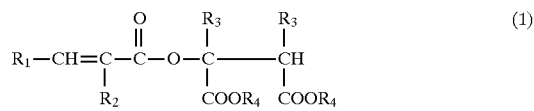

wherein $R_1$ is a hydrogen atom, —OH group, —$COOR_5$ group, or group expressed as:

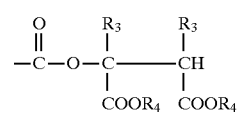

$R_2$ is a hydrogen atom, —$CH_3$ group, or —$CH_2COOR_4$ group, $R_3$ is a hydrogen atom, —OH group, or —$CH_2COOR_4$ group, $R_4$ is a hydrogen atom, sodium atom, potassium atom, or —$NH_4$ group, and $R_5$ is a sodium atom, potassium atom, or —$NH_4$ group; a polymer having a structure unit expresses as:

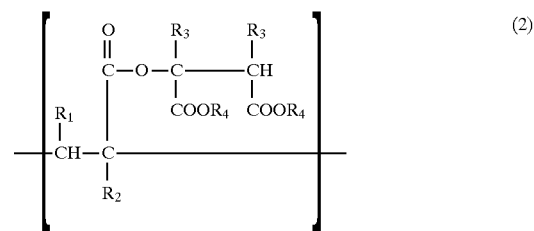

wherein $R_1$ through $R_5$ are identical with the above; and a composition containing a polymer that excels the conventional chleating agents in chleating and dispersing effects besides rendering excellent biodegradability. Therefore, the composition is preferably used as a detergent composition, an inorganic pigment dispersing agent, a fiber treatment agent, a water treatment agent (anti-scale agent), and a bleaching assistant for wood pulp, etc.

1 Claim, 8 Drawing Sheets ness of 5,859,286

MONOMER, POLYMER OF THE SAME, AND COMPOSITION CONTAINING THE POLYMER

FIELD OF THE INVENTION

The present invention relates to a new monomer, a polymer of the same, and a new composition containing the polymer. The composition is preferably used as a detergent composition, an inorganic pigment dispersing agent, a fiber treatment agent, a water treatment agent (anti-scale agent), a bleaching assist for wood pulp, etc.

BACKGROUND OF THE INVENTION

Various kinds of organic and inorganic chleating agents have been used as detergent compositions, dispersing agents, coagulating agents, water treatment agents (anti-scale agents), chleating reagents, fiber treatment agents, bleaching assistants for wood pulp, pH adjusting agents, detergents, etc.

Of all the chleating agents, polymers based on carboxylic acid (organic chleating agent), produced by polymerizing a monomer of maleic acid or acrylic acid, are known to render excellent chleating and dispersing effects on inorganic particles, and therefore have been used in diversified fields. Organic chleating agents, such as ethylenediaminetetraacetate and nitrilotriacetate, are known to render relatively high ability in effectively capturing heavy metal ions.

However, in the polymers based on carboxylic acid produced by polymerizing a monomer of maleic acid or acrylic acid, a carboxyl group bonds directly to the main chain, and for this reason, the main chain inhibits free rotation of the carboxyl group. Thus, such polymers based on carboxylic acid renders unsatisfactory ability in capturing metal ions, especially, heavy metal ions.

The organic chleating agents, such as ethylenediaminetetraacetate and nitrilotriacetate, capture a relatively small amount of metal ions per unit weight, and the dispersing effect of the same on inorganic particles is insufficient to meet the demand from all the uses (fields).

Thus, there has been an increasing need for a chleating agent suitably used in diversified fields, that is, a compound which has an excellent dispersing effect on inorganic particles, high heavy metal ion capturing ability besides being capable of capturing a large amount of metal ions per unit weight. In addition, such a chleating agent is expected to render excellent biodegradability.

SUMMARY OF THE INVENTION

It is therefore a first object of the present invention to provide a compound having all the above-explained abilities, that is, a new monomer suitably used as a raw material of a polymer, and a producing process of the same.

It is a second object of the present invention to provide a new polymer suitably used in diversified fields, and a producing process of the same.

It is a third object of the present invention to provide a new composition containing the above polymer.

The inventors of the present invention have performed researches in the hope to find a new monomer, a polymer of the same, and a new composition containing the polymer to achieve the above objects. In the meantime, the inventors found that a monomer having a specific structure is suitably used as a raw material of a polymer. Also, the inventors found that a polymer having this specific structure is soluble to water, renders an excellent dispersing effect on inorganic particles and high ability in capturing heavy metal ions, and captures a large amount of metal ions per unit weight. The inventors also acknowledged that the polymer renders excellent biodegradability. Further, the inventors found that a composition containing the above polymer is suitably used as a detergent agent, an inorganic pigment dispersing agent, a fiber treatment agent, a water treatment agent (anti-scale agent), bleaching assistant for wood pulp, etc.

To be more specific, a monomer of the present invention has a structure expressed as:

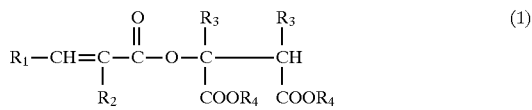

wherein $R_1$ is a hydrogen atom, —OH group, —COOR$_5$ group, or group expressed as:

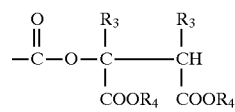

$R_2$ is a hydrogen atom, —CH$_3$ group, or —CH$_2$COOR$_4$ group, $R_3$ is a hydrogen atom, —OH group, or —CH$_2$COOR$_4$ group, $R_4$ is a hydrogen atom, sodium atom, potassium atom, or —NH$_4$ group, and $R_5$ is a sodium atom, potassium atom, or —NH$_4$ group.

According to the above structure, the monomer has a molecular structure having a plurality of carboxyl groups bonded away from the double bond. Thus, the monomer is suitably used as a raw material of the polymer having a specific structure unit.

A polymer of the present invention has a structure unit expressed as:

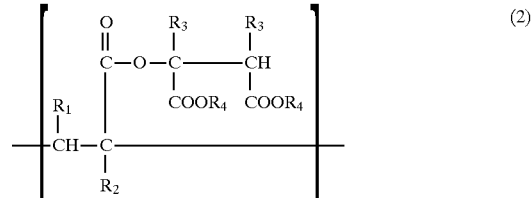

wherein $R_1$ is a hydrogen atom, —OH group, —COOR$_5$ group, or group expressed as:

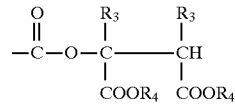

$R_2$ is a hydrogen atom, —CH$_3$ group, or —CH$_2$COOR$_4$ group, $R_3$ is a hydrogen atom, —OH group, or —CH$_2$COOR$_4$ group, $R_4$ is a hydrogen atom, sodium atom, potassium atom, or —NH$_4$ group, and $R_5$ is a sodium atom, potassium atom, or —NH$_4$ group.

According to the above structure, the polymer has a molecular structure including a plurality of carboxyl groups which are not directly bonded to the main chain, and for this reason, free rotation of carboxyl groups is not inhibited by the main chain. Thus, the polymer is soluble to water, and compared with conventional chleating agents, it renders an excellent dispersing effect on inorganic particles and high ability in capturing heavy metal ions, and captures a large amount of metal ions per unit weight. Also, the polymer renders excellent biodegradability. In short, the above polymer excels the conventional chleating agents in the chleating and dispersing effects besides rendering excellent biodegradability.

A composition of the present invention is characterized by containing the above polymer to fulfill the third object. According to the above structure, the composition contains a polymer that excels the conventional chleating agents in the chleating and dispersing effects besides rendering excellent biodegradability. For this reason, the above composition is suitably used as a detergent composition, an inorganic pigment dispersing agent, a fiber treatment agent, a water treatment agent (anti-scale agent), a bleaching assistant for wood pulp, etc.

For a fuller understanding of the nature and advantages of the invention, reference should be made to the ensuing detailed description taken in conjunction with the accompanying drawings.

DESCRIPTION OF THE EMBODIMENTS

Figure 1:
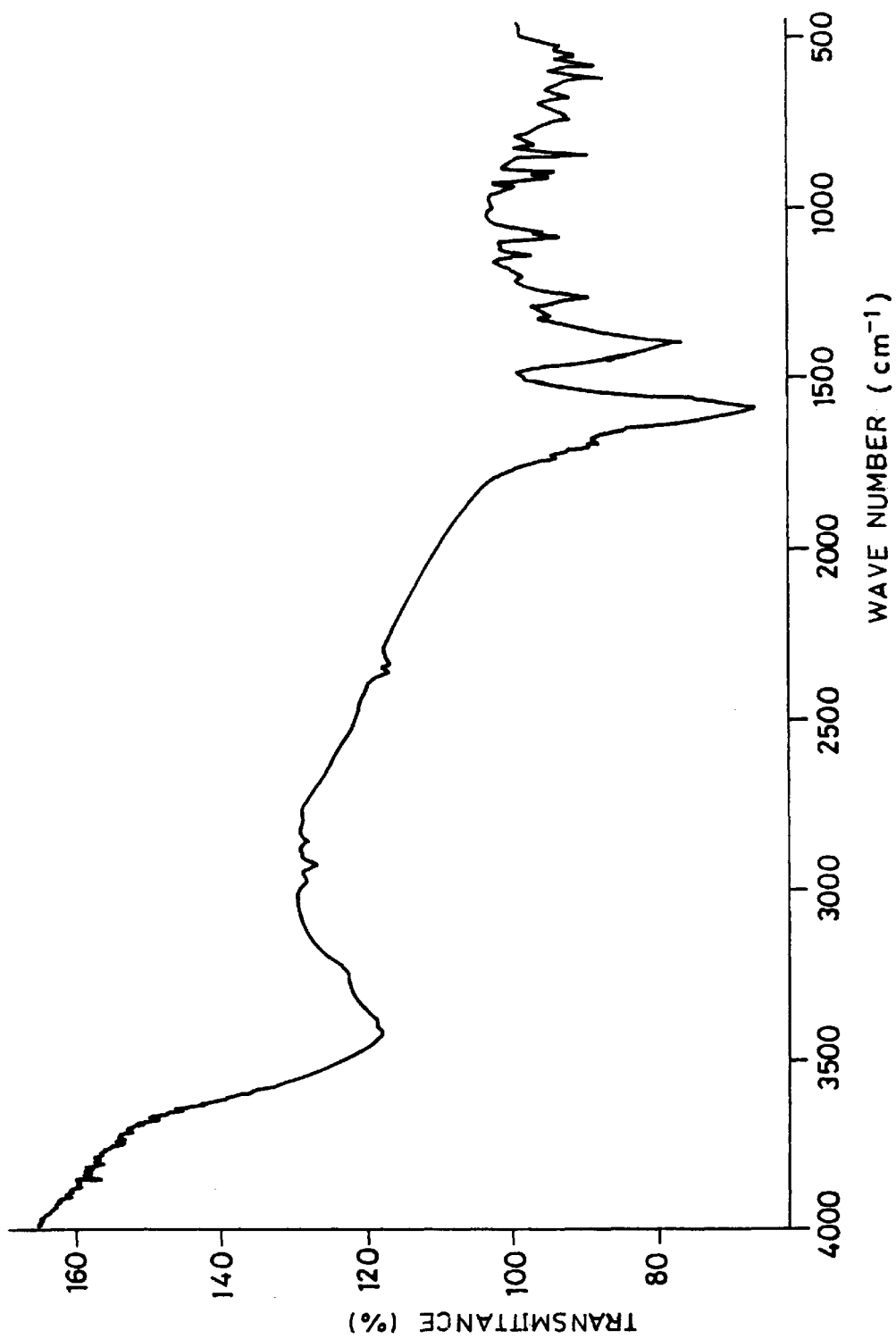
FIG. 1 shows an infrared absorption spectrum of a reaction product obtained in Example 1 of the present invention.

Following description will describe the present invention in detail.

A polymer of the present invention having a structure unit expressed by Formula (2) above is, but not limited to, a polymer whose substituent group represented by $R_1$ is a hydrogen atom, —OH group, —COOR$_5$ group, or group expressed as:

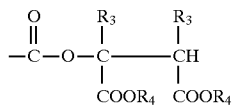

whose substituent group represented by $R_2$ is a hydrogen atom, —CH$_3$ group, or —CH$_2$COOR$_4$ group, whose substituent group represented by $R_3$ is a hydrogen atom, —OH group, or —CH$_2$COOR$_4$ group, whose substituent group represented by $R_4$ is a hydrogen atom, sodium atom, potassium atom, or —NH$_4$ group, and whose substituent group represented by $R_5$ is a sodium atom, potassium atom, or —NH$_4$ group. The weight average molecular weight (Mw) of the polymer is preferably in a range between 300 and 8,000,000.

Also, a monomer used as a raw material of the polymer of the present invention, which is expressed by Formula (1) above, is, but not limited to, a monomer whose substituent groups respectively represented by $R_1$ through $R_4$ are identical with those explained in the above paragraph. The above monomer is produced by reacting ethylenic unsaturated carboxylic acid with poly carboxylic acid containing a hydroxyl group.

Examples of ethylenic unsaturated carboxylic acid are: unsaturated monocarboxylic acids, such as (meta)acrylic acid, α-hydroxyacrylate, and crotonic acid, and salts and ester compounds of these acids; and unsaturated poly carboxylic acids, such as maleic acid, maleic anhydride, fumaric acid, itaconic acid, citraconic acid, and aconitic acid, and satls and ester compounds of these acids; etc. Examples of the above ester compounds are methyl acrylate, methyl methacrylate, methyl maleate, etc. One or more than one of these compounds is used as occasion demands.

Examples of the poly carboxylic acid containing a hydroxyl group are citric acid, malic acid, tartaric acid, succinic acid, salts and hydrates of these acids, etc. One or more than one of these compounds is used as occasion demands.

Of all these examples, maleic anhydride and citric acid are preferable for ethylenic unsaturated carboxylic acid and poly carboxylic acid containing a hydroxyl group, respectively. The reason why is as follows. Maleic anhydride and citric acid are readily esterified, and when a resulting monomer, or ester compound, is subject to polymerization, a resulting polymer renders excellent physical properties as a chleating agent. Also, transesterifcation of ethylenic unsaturated carboxylic acid (ester compound) with poly carboxylic acid containing a hydroxyl group yield a highly pure monomer.

During the above reaction, a solvent may be added to the reactant as occasion demands. Any solvent will do as long as it does not inhibit with the reaction, and examples of which are organic solvents, such as benzene, toluene, xylene, monochlorobenzene, dichlorobenzene, methylene chloride, hexane, cyclohexane, acetone, methylethylketone, and dimethylformaimde. An adding amount of the solvent is not especially limited. Note that in case that maleic anhydride is used as ethylenic unsaturated carboxylic acid, it is preferable not to use any solvent during the esterification to enhance the yield of the monomer.

In addition, a catalyst may be used in the above reaction. Any catalyst will do, and examples of which are mineral acids, such as hydrochloric acid, sulfuric acid, and nitric acid; organic acids, such as p-toluenesulfonic acid; solid acids, such as heteropoly acid; acid-type ion exchange resins; etc.

The reaction temperature of the above esterification is not especially limited, but preferably in a range between 10° C. and 180° C., and more preferably in a range between 50° C. and 160° C. to enhance the yield of the monomer. The reaction time, such that is necessary to complete the above reaction in a satisfactory manner, can be determined depending on the kinds, combination, a used amount of ethylenic unsaturated carboxylic acid, poly carboxylic acid containing a hydroxyl group, solvent, and catalyst, or the reaction temperature. A reaction pressure is not especially limited, and the reaction can take place under normal (atmospheric), reduced, or applied pressure.

A resulting monomer of the above reaction readily polymerizes, and a polymerization inhibitor, such as hydroquinone, may be added to prevent the polymerization. Further, in case that maleic acid and/or maleic anhydride are used as ethylenic unsaturated carboxylic acid in the above reaction, a metal compound, such as ferrous ammonium sulfate may be added to prevent the coloring of the resulting monomer.

A monomer expressed by Formula (1) above whose substituent group represented by $R_4$ is a sodium atom, potassium atom, or —NH$_4$ group is readily produced in the following manner: ethylenic unsaturated carboxylic acid is reacted with poly carboxylic acid containing a hydroxyl group, and a resulting compound is treated with, for example, a sodium hydroxide water solution, potassium hydroxide water solution, or aqueous ammonia, etc. Note that the treatment method is not especially limited.

As has been explained, the monomer of the present invention has a structure expressed by Formula (1) above. A polymer of the present invention is readily produced by a process of reacting ethylenic unsaturated carboxylic acid with poly carboxylic acid containing a hydroxyl group. Since the monomer has a structure having a plurality of carboxyl groups bonded away from the double bond, it can be suitably used as, for example, a raw material for a chleating polymer soluble to water.

Next, a polymer of the present invention can be readily produced by letting a polymer expressed by Formula (1) above alone undergo polymerization or copolymerizing the same with a monomeric ingredient containing an ethylenic unsaturated monomer capable of copolymerizing with the monomer.

It is preferable that the above ethylenic unsaturated monomer is soluble to water. More specifically, a preferable ethylenic unsaturated monomer renders solubility of 5 g or more in 100 g of water at 100° C. A ratio of a monomer expressed by Formula (1) above to the ethylenic unsaturated monomer is such that makes a mole ratio of the former to a total of the former and the latter 1/100 or more and less than 1/1.

The weight average molecular weight of a polymer of the present invention is preferably in a range between 300 and 8,000,000, more preferably in a range between 500 and 100,000, and most preferably in a range between 1,000 and 20,000. In particular, when the polymer, that is, a resulting composition, is used as a detergent composition (detergent builder), the range between 500 and 100,000 is preferable, and a range between 3,000 and 15,000 is more preferable. The weight average molecular weight out of the above range is not preferable because a composition containing such a polymer renders poor physical properties.

Examples of the ethylenic unsaturated monomer are: unsaturated monocarboxylic acids, such as (meta)acrylic acid, α-hydroxyacrylic acid, and crotonic acid, and salts of these acids; unsaturated poly carboxylic acids, such as maleic acid, maleic anhydride, fumaric acid, itaconic acid, citraconic acid, aconitic acid, and salts of these acids; vinyl acetate; etc.

Also, the ethylenic unsaturated monomer may be an unsaturated compound containing a hydroxyl group expressed as:

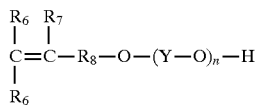 (3)

where each of $R_6$ and $R_7$ is a hydrogen atom or —CH$_3$ group but both $R_6$ and $R_7$ are not —CH$_3$ groups at the same time, $R_8$ is —CH$_2$—, —(CH$_2$)$_2$—, or —C(CH$_3$)$_2$—, $R_6$, $R_7$, and $R_8$ have 3 carbon atoms in total, Y is an alkylene group having 2 or 3 carbon atoms, and n is an integer in a range between 0 and 100. Examples of such an unsaturated compound containing a hydroxyl group are 3-methyl-3-butene-1-ol(isoprenol), 3-methyl-2-butene-1-ol(prenol), and 2-methyl-3-butene-2-ol(isoprene alcohol). Also, a compound produced by adding 1–100 mole of ethyleneoxide and/or propyleneoxide to 1 mole of any of these example compounds may be used as the ethylenic unsaturated monomer.

Further, the ethylenic unsaturated monomer may be: a compound expressed as:

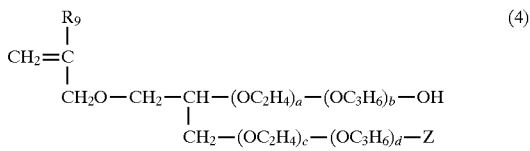 (4)

where $R_9$ is a hydrogen atom or —CH$_3$ group, a, b, c, and d are respectively integers ranging from 0 to 100 and a+b+c+d=0–100, the bond order of —OC$_2$H$_4$— and —OC$_3$H$_6$— is not limited, Z is a hydroxyl group, sulfonic group, or phosphoric group when c+d=0 and a hydroxyl group when c+d=1–100, an example of such a compound including:

3-alloxy-2-hydroxypropanesulfonic acid and a salt thereof;

glycerol monoallylether, and a compound based on unsaturated (meta)allylether, such as a compound produced by adding 1–100 mole of ethyleneoxide and/or propyleneoxide to 1 mole of glycerol monoallyether;

compounds containing an unsaturated sulfonic group, such as vinyl sulfonic acid, allylsulfonic acid, methallylsulfonic acid, styrenesulfonic acid, 2-acrylamide-2-methylpropanesulfonic acid, sulfoethyl(meta)acrylate, sulfopropyl(meta)acrylate, 2-hydroxysulfopropyl (meta)acrylate, and sulfoethylmaleimide, and salts thereof;

ester of an alcohol prepared by adding 0–100 mole of ethyleneoxide and/or propyleneoxide to alkylalcohol having up to 20 carbon atoms, and monocarboxylic acid, such as (meta)acrylic acid and crotonic acid, monoester of the above-prepared alcohol and poly carboxylic acid, such as maleic acid, fumaric acid, itaconic acid, citraconic acid, and aconitic acid, salts of these monoesters, and an unsaturated compound based on alkyl-terminated ester, such as diester; and an ester-based compound produced by adding 1–100 mole of ethyleneoxide and/or propyleneoxide to 1 mole of unsaturated carboxylic acid, such as (meta)acrylic acid and crotonic acid, a monoester-based compound produced by adding 1–100 mole of ethyleneoxide and/or propyleneoxide to 1 mole of unsaturated carboxylic acid, such as maleic acid, fumaric acid, itaconic acid, citraconic acid, and aconitic acid, salts of these monoester-based compounds, and an unsaturated ester-based compound, such as diester-based compound.

One or more than one of these ethylenic unsaturated monomers is used as occasion demands. Of all these examples, the most preferable are (meta)acrylic acid and (meta)acrylate because they readily polymerize and the their respective resulting polymers render excellent physical properties.

Examples of a polymerization initiator used in producing a polymer of the present invention include, but are not limited to: hydrogen peroxide; persulfates, such as ammonium persulfate, sodium persulfate, and potassium persulfate; 2,2'-azobis(2-amidino propane)hydrochloride; azo-based compounds, such as 4,4'-azobis(4-cyanovaleric acid), 2,2'-azobis(isobutyronitrile), 2,2'-azobis(4-methoxy-2,4-dimethylvaleronitrile); organic peroxides, such as benzoyl peroxide, lauroyl peroxide, peracetic acid, persuccinic acid, di-t-butylperoxide, t-butylhydroperoxide, and cumenehydroperoxide; etc. One or more than one of these polymerization initiators is used as occasion demands.

During the polymerization, a pH of the reactant solution can be of any value; however, since the monomer is acid, it is preferable to neutralize the reactant solution using a basic compound to promote the reaction. Examples of preferred basic compounds for neutralization are: hydroxides or carbonates of alkaline metals, such as sodium, potassium, and lithium; ammonia; alkylamines, such as monomethylamine, dimethylamine, trimethylamine, monoethylamine, diethylamine, triethylamine; alkanolamines, such as monoethanolamine, diethanolamine, triethanolamine, isopropanolamine, isobutanolamine; pyridine; etc. One or more than one of these basic compounds is used as occasion demands.

Letting a monomer undergo polymerization in the presence of polyvalence metal ions can reduce an amount of residual monomer in the reactant solution, thereby narrowing the molecular weight distribution of the resulting polymer. The polyvalence metal ions are iron ions, ions containing vanadium atoms, copper ions, etc. Of all these examples, $Fe^{3+}$, $Fe^{2+}$, $Cu^{+}$, $Cu^{2+}$, $V^{2+}$, $V^{3+}$, and $VO^{2+}$ are preferable, and $Fe^{3+}$, $Cu^{2+}$, and $VO^{2+}$ are particularly preferable. One or more than one kind of these polyvalence metal ions are used as occasion demands.

A preferable concentration of the polyvalence metal ions with respect to a whole amount of the reactant solution is in a range between 0.1 ppm and 100 ppm. A concentration lower than 0.1 ppm is not preferable because the above-explained effect is hardly realized. A concentration exceeding 100 ppm is not preferable either because, for example, a copolymer based on maleic acid, produced as a result of copolymerization of a monomer based on maleic acid, shows some color and such a colored monomer can not be used as detergent composition or the like. Note that a polymer produced in the presence of polyvalence metal ions renders excellent iron ion capturing ability (iron powder anti-depositing ability), and therefore, can be preferably used as detergent compositions.

A process of letting the polyvalence metal ions be present in the reactant solution is not especially limited. An example process is to add metal compounds or metals that can be ionized in a reactant solution to the reactant solution. Examples of the metal compounds or metals include, but are not limited to:

water-soluble metallic salts, such as vanadium oxytrichloride, vanadium trichloride, vanadium oxalate, vanadium sulfate, vanadic anhydride, ammonium methavanadate, hypovanadus ammonium sulfate [$(NH_4)_2SO_4 \cdot VSO_4 \cdot 6H_2O$], vanadus ammonium sulfate [$(NH_4)V(SO_4)_2 \cdot 12H_2O$], copper (II) acetate, copper (II) bromide, bis(acetylacetonato)copper (II), cupric chloride, ammonium copper chloride, copper carbonate, copper (II) chloride, copper (II) citrate, copper (II) formate, copper (II) hydroxide, copper nitrate, copper naphthenate, copper (II) oleate, copper maleate, copper phosphate, copper (II) sulfate, cuprous chloride, copper (I) cyanide, copper iodide, copper (I) oxide, copper thiocyanate, iron acetylacetonate, iron ammonium citrate, ferric ammonium oxalate, ferrous ammonium sulfate, ferric ammonium sulfate, iron citrate, iron fumarate, iron maleate, ferrous lactate, ferric nitrate, iron pentacarbonyl, ferric phosphate, and ferric pyrophosphate;

metal oxides, such as vanadium pentoxide, copper (II) oxide, cuprous oxide, and cupric oxide;

metal sulfates, such as copper (II) sulfate and iron sulfate;

copper powders and iron powders; etc.

Examples of an aqueous medium used in the above polymerization include, but are not limited to:

water;

alcohols, such as methanol, ethanol, and propanol;

ethers, such as diethylether;

cellosolves, such as ethyl cellosolve and n-butylcellosolve;

ketones, such as methylketone; etc.

Conditions for the above polymerization are: the reaction temperature is approximately 100° C., and a reaction time is approximately 180 minutes. However, these conditions may be changed depending on the kinds and amounts of the monomer, catalyst, and aqueous medium. A reaction pressure is not especially limited, and the reaction can take place in normal (atmospheric), reduced, or applied pressure.

As has been explained, the polymer of the present invention has a structure unit expressed by Formula (2) above. As is apparent from the structure unit expressed by Formula (2) above, the polymer includes a plurality of atom groups each having 2–4 carboxyl groups, and the atom groups are bonded to the main chain in such a manner that there exit at least 3 atoms between a carbon atom forming the carboxyl group and a carbon atom forming the main chain, which is expressed as —C—O—C—. Further, as is apparent from the structure unit expressed by Formula (2) above, the polymer includes a plurality of atom groups each having 2–4 carboxyl groups, and the atom groups are bonded to the main chain in such a manner that there exits an ester linkage between a carbon atom forming the carboxyl group and a carbon atom forming the main chain, which is expressed as —COO—. Also, as is apparent from the composition of the monomeric ingredient, a ratio of the atom groups to the whole polymer of the present invention is 5 percent by weight or more.

Therefore, the polymer has a molecular structure having a plurality of carboxyl groups which are not directly bonded to the main chain, and for this reason, the free rotation of the carboxyl groups are not interfered by the main chain.

Thus, the above polymer is soluble to water and, compared with the conventional chleating agents, it an renders excellent dispersing effect on inorganic particles and high ability in capturing heavy metal ions, and captures a large amount of metal ions per unit weight. In addition, the polymer renders excellent biodegradability. In short, the above polymer excels the conventional chleating agents in chleating and dispersing effects besides rendering excellent biodegradability.

The polymer of the present invention shows the physical properties as follow:

(A) biodegradability ratio: 40% or more calcium ion capturing ability: 200 mgCaCO$_3$/g or more calcium ion stability constant: 4.0 or more iron ion capturing ability: 9.0 or more clay dispersing ability: 0.5 or more (B) biodegradability ratio: 10% or more calcium ion capturing ability: 350 mgCaCO$_3$/g or more calcium ion stability constant: 4.2 or more clay dispersing ability: 0.5 or more The calcium ion capturing ability referred herein is defined as a value (mgCaCO$_3$/g), converted into an amount of calcium carbonate, representing an amount of calcium ions captured by 1 g of the polymer. The calcium ion capturing ability indicates a degree of detergency of a detergent composition containing the above polymer, which will be explained below, and the larger the value, the higher the ability. A polymer having a calcium ion capturing ability of less than 200 mgCaCO$_3$/g is not preferable, because it does not show satisfactory ability when used as a detergent composition, an inorganic pigment dispersing agent, a fiber treatment agent, etc.

The calcium ion stability constant referred herein is a value representing the ability of chleating calcium ions in water, and the larger the value, the higher the ability. To be more specific, in case a polymer having a high calcium ion stability constant is used as a detergent composition, it shows excellent ability of removing dirt from fibers by removing calcium ions existing in the dirt during the washing. A polymer having a calcium ion stability constant of less than 4.0 is not preferable, because it does not show satisfactory ability when used as a detergent composition or the like.

The iron ion capturing ability referred herein is a value representing the ability of capturing iron ions in water, and the larger the value, the higher the ability. To be more specific, in case a polymer having high iron ion capturing ability is used as a detergent composition, it shows excellent ability in preventing the clothes from becoming yellow-tinted during the washing. Preferred iron ion capturing ability is 11.0 or more and more preferably, 13.0 or more. A polymer having the iron ion capturing ability of less than 9.0 is not preferable, because it does not show satisfactory ability when used as a detergent composition or the like.

The clay dispersing ability referred herein is represented by suspension degree of a supernatant of a suspension liquid of clay after it has been let stand for a predetermined period, and the larger the value, the higher the ability. To be more specific, in case a polymer having high clay dispersing ability is used as a detergent composition, it shows excellent ability in removing dirts or the like from the fibers and dispersing the removed dirts in water during the washing. Preferred clay dispersing ability is 1.2 or more, and clay dispersing ability of 1.4 or more is further preferable to prevent the dirt deposition. A polymer having the clay dispersing ability of less than 0.5 is not preferable, because it does not show satisfactory ability when used as a detergent composition or the like.

Evaluation methods of the biodegradability, calcium ion capturing ability, calcium ion stability constant, iron ion capturing ability, and clay dispersing ability will be explained in detail in Example 5 below.

The polymer of the present invention is produced by polymerizing a monomeric ingredient containing a monomer expressed by Formula (1) above using an aqueous medium.

Accordingly, it has become possible to readily produce a polymer having a molecular structure including a plurality of carboxyl groups which are not directly bonded to the main chain. Thus, the above producing process can produce a polymer that excels the conventional chleating agents in chleating and dispersing effects besides rendering excellent biodegradability.

Next, a composition of the present invention will be described below. The composition of the present invention contains the above polymer, and is used for, for example, a detergent composition, an inorganic pigment dispersing agent, a fiber treatment agent, a water treatment agent (anti-scale agent), a bleaching assistant for wood pulp, etc. The composition will be described more in detail below.

The detergent composition comprises the above polymer, a surfactant, and if necessary, an enzyme. A preferred ratio of the polymer to the whole detergent composition is in a range between 0.1 percent by weight and 20 percent by weight, and a range between 0.5 percent by weight and 15 percent by weight is more preferable. Also, preferred surfactants are an anionic surfactant, a nonionic surfactant, an amphoteric surfactant, and a cationic surfactant.

Examples of the anionic surfactant are alkylbenzene sulfonate, alkyl ether sulfate, alkenyl ether sulfate, alkyl sulfate, alkenyl sulfate, $\alpha$-olefin sulfonate, salt of $\alpha$-sulfo fatty acid, salt of $\alpha$-sulfo fatty acid ester salt, alkane sulfonate, saturated or salt of unsaturated fatty acid, alkylether carboxylate, alkenyl ether carboxylate, amino acid type surfactant, N-acylamino acid type surfactant, alkyl phosphate ester and a salt thereof, alkenyl phosphate ester and a salt thereof, etc.

Examples of the nonionic surfactant are polyoxyalkylenealkylether, polyoxyalkylenealkenylether, polyoxyethylenealkylphenylether, alkanolamide higher fatty acid and alkyleneoxide-appended alkanolamide higher fatty acid alkanolamide, cone sugar fatty acid ester, alkyglycoside, glycerol fatty acid monoester, alkylamineoxide, etc.

Examples of the amphoteric surfactant are carboxyl type and sulfobetain type amphoteric surfactants, etc. Examples of the cationic surfactant are quaternary ammonium salt, etc.

A preferable ratio of the surfactant to the detergent composition is in a range between 5 percent by weight and 70 percent by weight, and more preferably, in a range between 20 percent by weight and 60 percent by weight.

Examples of the enzyme are protease, lipase, cellulase, etc. In particular, protease, alkali lipase, and alkali cellulase are preferred because they are highly active in an alkali cleaning liquid. A preferable ratio of the enzyme to the detergent composition is in a range between 0.01 percent by weight and 5 percent by weight. A ratio of the enzyme out of the above range breaks the balance between the enzyme and the surfactant, thereby making it impossible to upgrade the detergency.

The detergent composition may further include an alkali builder, a chelate builder, an anti-redepositing agent, a fluorescent agent, bleach, perfume, etc., all of which are known as typical ingredients contained in the detergent composition. The alkali builder includes silicate, carbonate, sulfate, etc. The chelate builder includes diglycol acid, oxycarboxylate, EDTA (ethylene diamine tetraacetic acid), DTPA (diethylenetriaminehexaacetic acid), citric acid, etc. Zeolite may be added to further upgrade the detergency.

The fiber treatment agent includes, as occasion demands, at least one ingredient selected from a group consisting of a dye agent, a peroxide, and a surfactant besides the polymer. The fiber treatment agent can be used in the steps of boiling-off, dying, bleaching, and soaping during the fiber treatment process. Note that any dye agent, peroxide and surfactant contained in a known fiber treatment agent are applicable.

In case the polymer is a copolymer based on maleic acid, 0.1–100 parts by weight of the dye agent, peroxide, and surfactant to the polymer are added to 1 part by weight of the polymer to upgrade the whiteness, color consistency, and color fastness of the fiber. Examples of fibers that can be used with the fiber treatment agent include, but are not limited to: cellulose-based fibers, such as cotton and hemp; chemical fibers, such as polyamide and polyester; animal fibers such as wool and silk; semisynthetic fibers, such as artificial silk; and a woven fabric or mixed fiber of these examples.

For example, when a fiber treatment agent including a copolymer based on maleic acid as the polymer is used in the boiling-off step, the fiber treatment agent preferably includes a known alkali agent and a known surfactant. When such a fiber treatment agent is used in the bleaching step, the fiber treatment agent preferably includes a peroxide and a chemical based on silicic acid, such as sodium silicate serving as a decomposition inhibitor of an alkaline bleaching agent.

The inorganic pigment dispersing agent includes, as occasion demands, polymerized phosphoric acid and a salt thereof, phosphonic acid and a salt thereof, polyvinyl alcohol, and anionizing denaturated polyvinyl alcohol besides the polymer.

The inorganic pigment dispersing agent disperses the inorganic pigments in clay or heavy or soft calcium carbonate used in paper coating. To be more specific, a stable, low-viscous, high-fluid, high-concentrated inorganic pigment slurry whose physical properties do not vary over time, such as high-concentrated calcium carbonate slurry, can be produced in the following manner: a slight amount of the inorganic pigment dispersing agent is added to an inorganic pigment, and the resulting inorganic pigment is dispersed in water. A preferable amount of the inorganic pigment dispersing agent is in a range between 0.05 part by weight and 2.0 parts by weight with respect to 100 parts by weight of an inorganic pigment.

The water treatment agent includes, as occasion demands, polymerized phosphate, phosphonate, an anti-corrosive agent, a slime controlling agent, and a chelating agent besides the polymer. The water treatment agent effectively prevents the scales in a cool water circulation system, a boiler water circulation system, a seawater desalting unit, a pulp digester, a black liquor evaporator, etc.

The bleaching assistant for wood pulp contains the polymer. The bleaching assistant may be used as a pre-treatment agent when bleaching the wood pulps or during the bleaching together with hydrogen peroxide, a chlorine-based bleaching agent, ozones, etc.

As has been explained, the composition of the present invention has a structure containing the above polymer. To be more specific, the composition contains a polymer that excels the conventional chleating agents in chleating and dispersing effects besides rendering excellent biodegradability. Thus, the composition is suitably used as a detergent composition, an inorganic dispersing agent, a fiber treatment agent, a water treatment agent (anti-scale agent), a bleaching assistant for wood pulp, etc.

The following description will describe examples and comparative examples of the present invention. However, the present invention is not limited to the description below. Note that in the following, "part(s)" means part(s) by weight.

(EXAMPLE 1)

To begin with, 196 parts of maleic anhydride serving as ethylenic unsaturated carboxylic acid, 420 parts of citric acid monohydrate serving as poly carboxylic acid containing a hydroxyl group, 3 parts of p-toluenesulfonic acid serving as a catalyst, and 0.01 part of ferrous ammonium sulfate hexahydrate serving as a metal compound are stirred in a four-neck 1 l-flask equipped with a thermometer, a stirring instrument and a reflux condenser and the reaction solution is heated to 140° C. and let stand for 30 minutes at 140° C.

Then, the reactant solution is cooled to 80° C. and 93.75 parts of 48 wt % sodium hydroxide water solution serving as a basic compound and 406.3 parts of pure water serving as an aqueous medium are added, and the resulting reactant solution is subject to stirring for 30 minutes. As a result, a water solution containing a water-soluble compound is obtained. Then, water, the catalyst and metal compound are removed from the reactant solution to obtain a compound.

Figure 2:
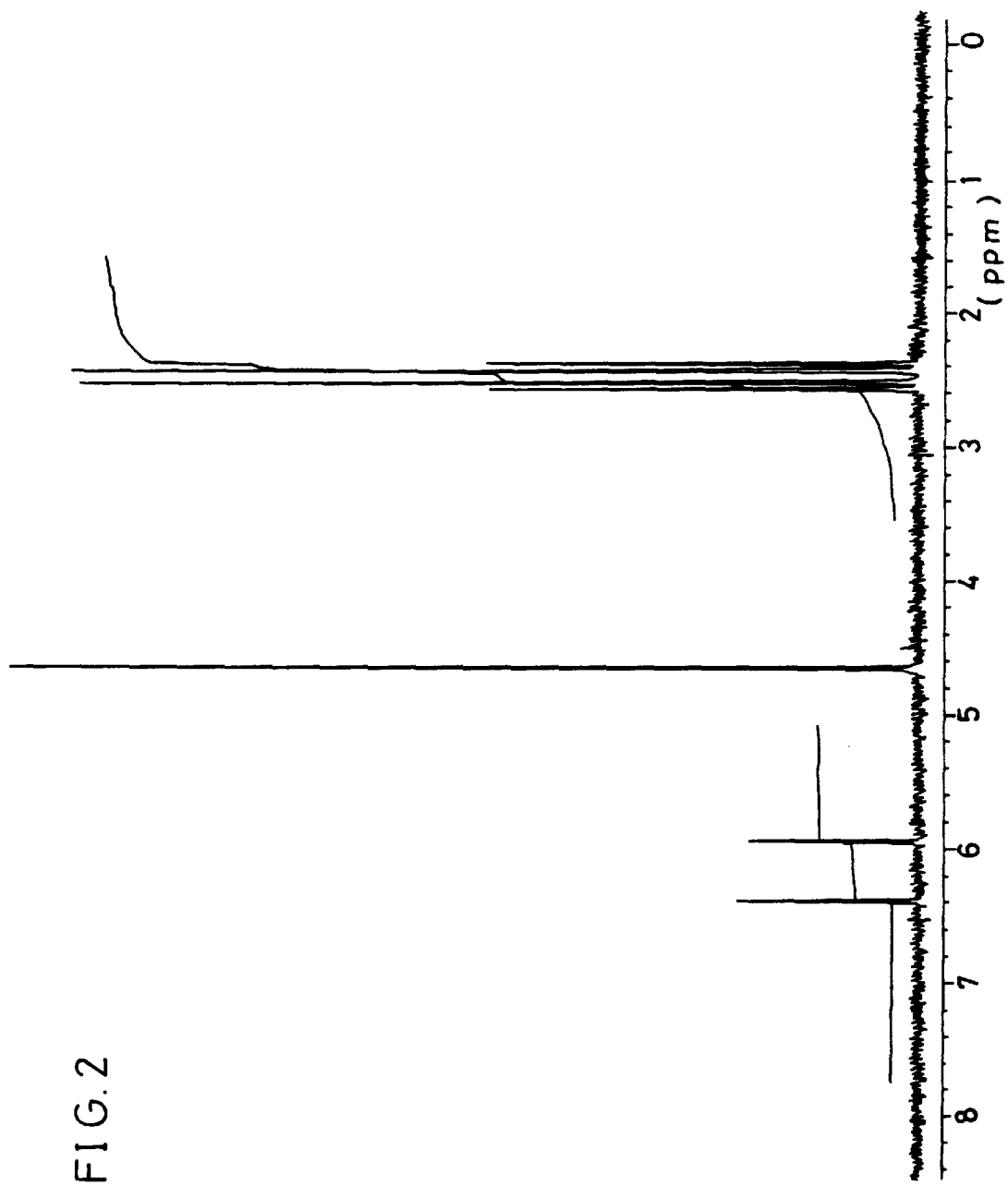
FIG. 2 shows a $^1$H-NMR chart of the above reaction product.

Next, $^1$H-NMR and infrared absorption spectrum (IR) of the water-soluble compound thus obtained are evaluated to identify the same. As a result, it is acknowledged that the resulting product, or the water-soluble compound, is a new monomer of the present invention. The infrared absorption spectrum and $^1$H-NMR of the resulting monomer are set forth in FIGS. 1 and 2, respectively.

(EXAMPLE 2)

The reaction and operation are carried out in the same manner as Example 1 except that 300 parts of tartaric acid is used instead of 420 parts of citric acid monohydrate as poly carboxylic acid containing a hydroxyl group, and a water-soluble compound is obtained.

Figure 3:
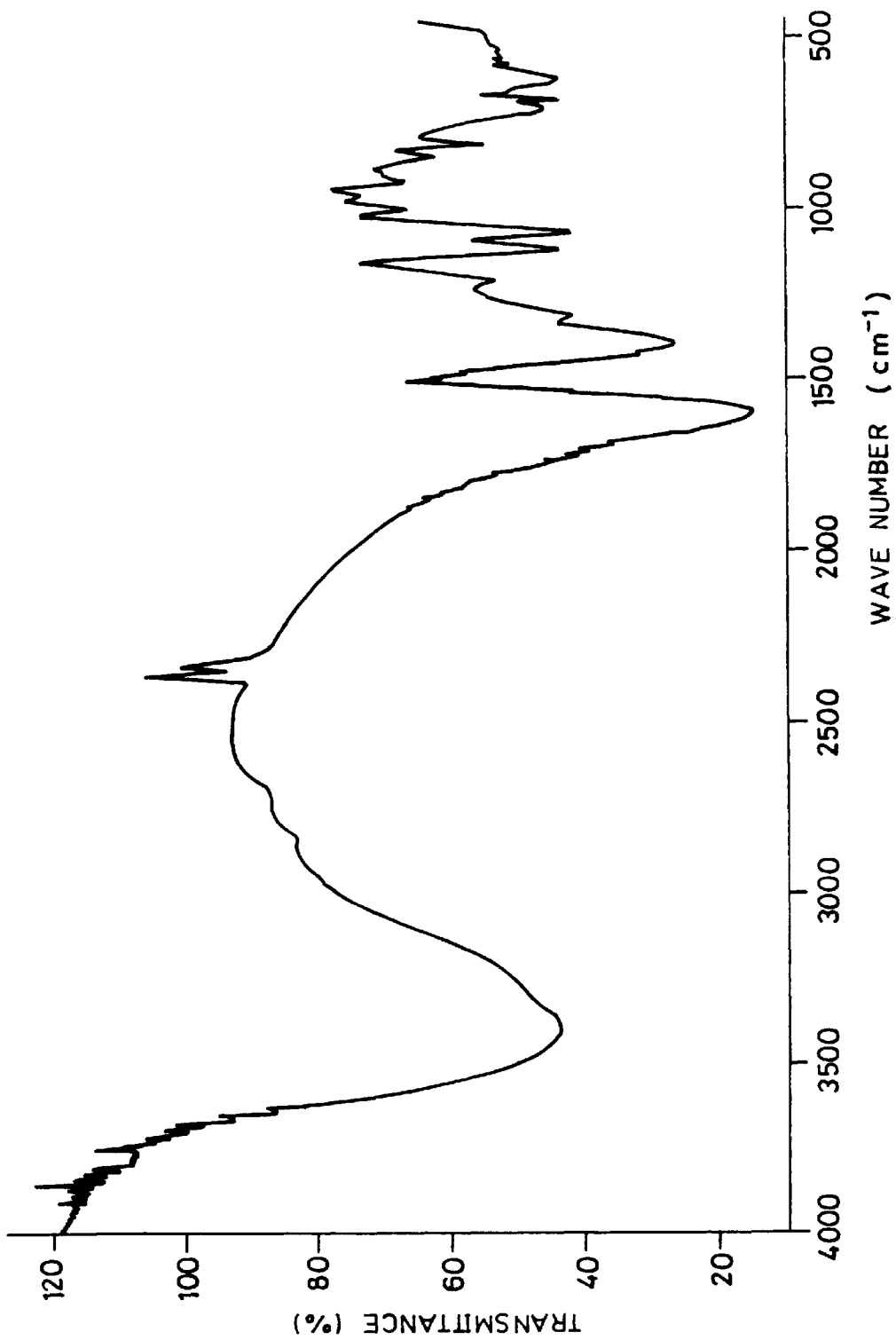
FIG. 3 shows an infrared absorption spectrum of a reaction product obtained in Example 2 of the present invention.
Figure 4:
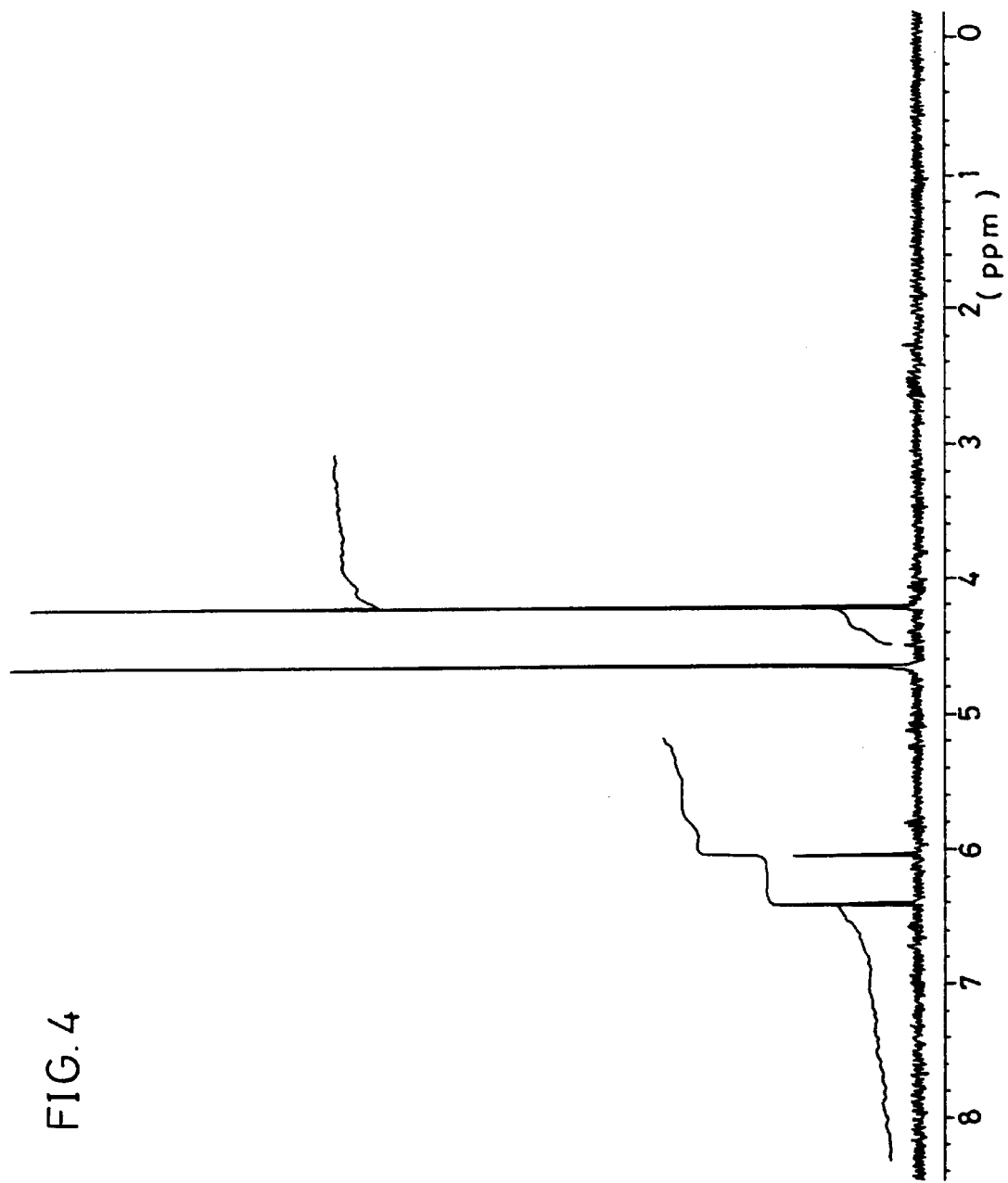
FIG. 4 shows a $^1$H-NMR chart of the reaction product of FIG. 3.

The water-soluble compound thus obtained is identified, in the same manner as Example 1, to be a new monomer of the present invention. The infrared absorption spectrum and $^1$H-NMR of the resulting monomer are set forth in FIGS. 3 and 4, respectively.

(EXAMPLE 3)

The reaction and operation are carried out in the same manner as Example 1 except that 268 parts of tartaric acid is used instead of 420 parts of citric acid monohydrate as poly carboxylic acid containing a hydroxyl group, and a water-soluble compound is obtained.

Figure 5:
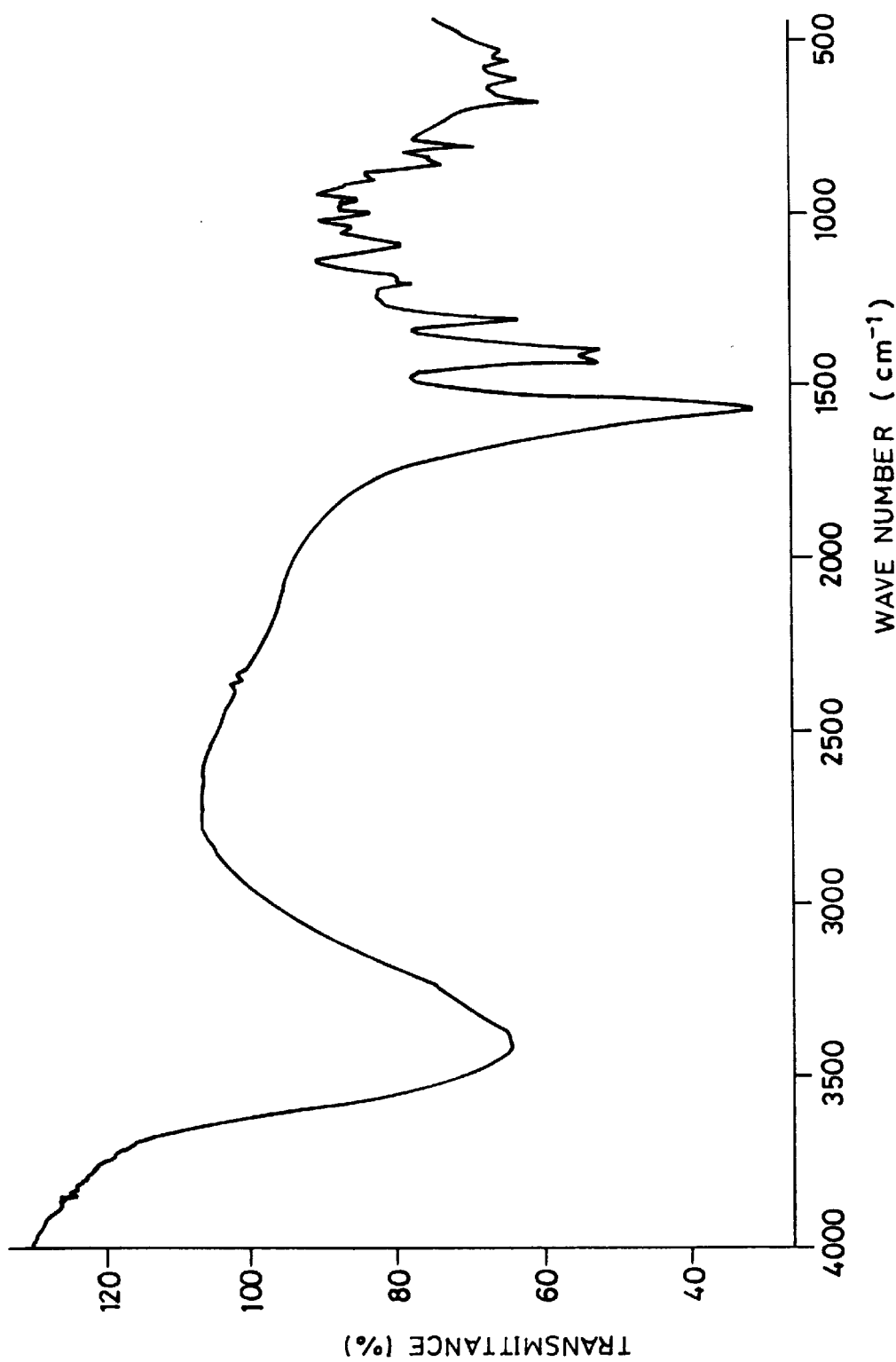
FIG. 5 shows an infrared absorption spectrum of a reaction product obtained in Example 3 of the present invention.
Figure 6:
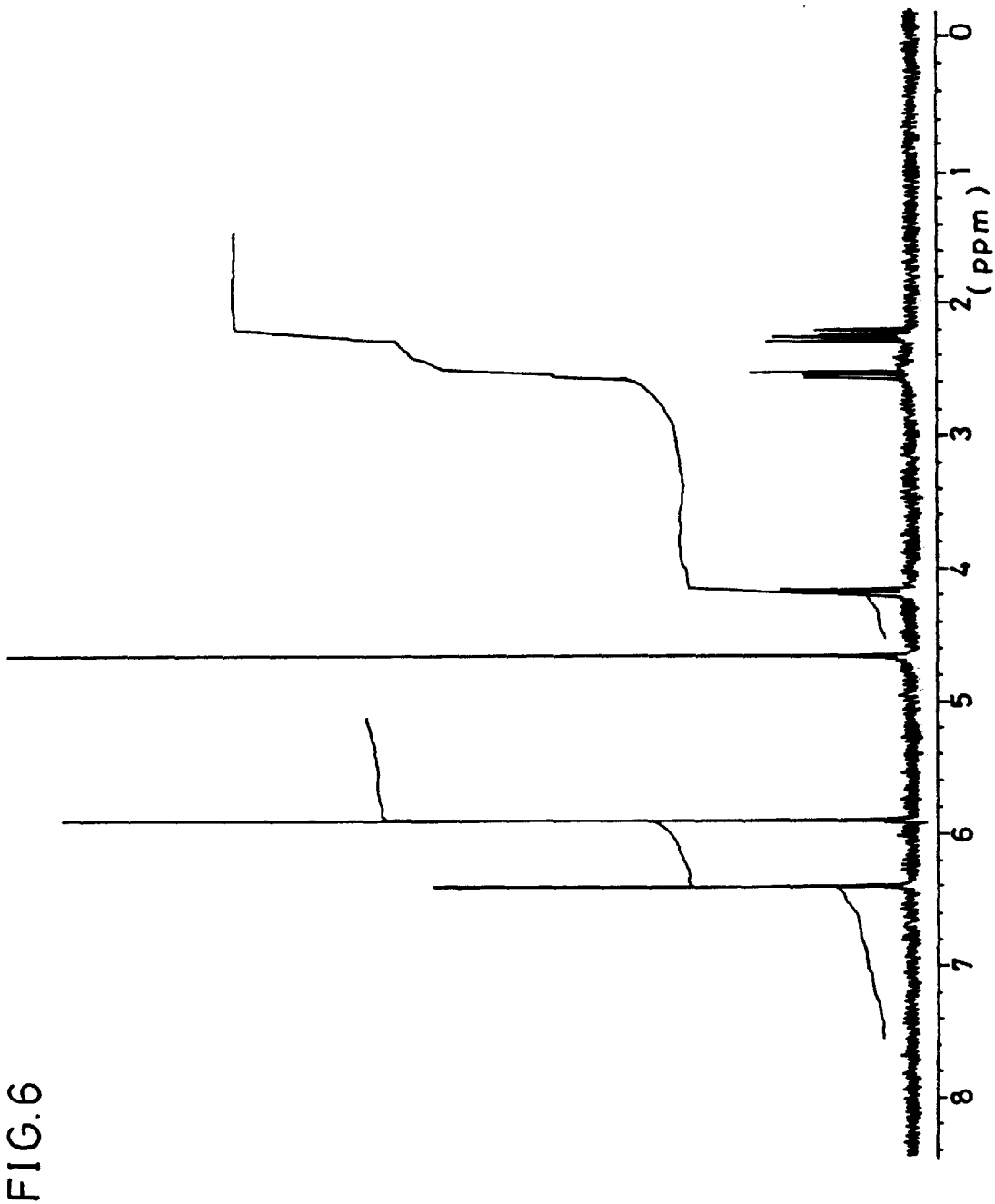
FIG. 6 shows a $^1$H-NMR chart of the reaction product of FIG. 5.

The water-soluble compound thus obtained is identified, in the same manner as Example 1, to be a new monomer of the present invention. The infrared absorption spectrum and $^1$H-NMR of the resulting monomer are set forth in FIGS. 5 and 6, respectively.

(EXAMPLE 4)

To begin with, 500 parts of dimethylformamide serving as a solvent, 172 parts of methyl acrylate serving as ethylenic unsaturated carboxylic acid, 420 parts of citric acid monohydrate, 3 parts of p-toluenesulfonic acid, and 0.035 part of hydroquinone serving as a polymerization inhibitor are stirred in a four-neck 1 l-flask equipped with a thermometer, a stirring instrument and a reflux condenser at 100° C. for 30 minutes while removing a by-product, namely, methanol.

Then, the reactant solution is heated under reduced pressure to remove dimethylformamide to obtain a reactant product.

Figure 7:
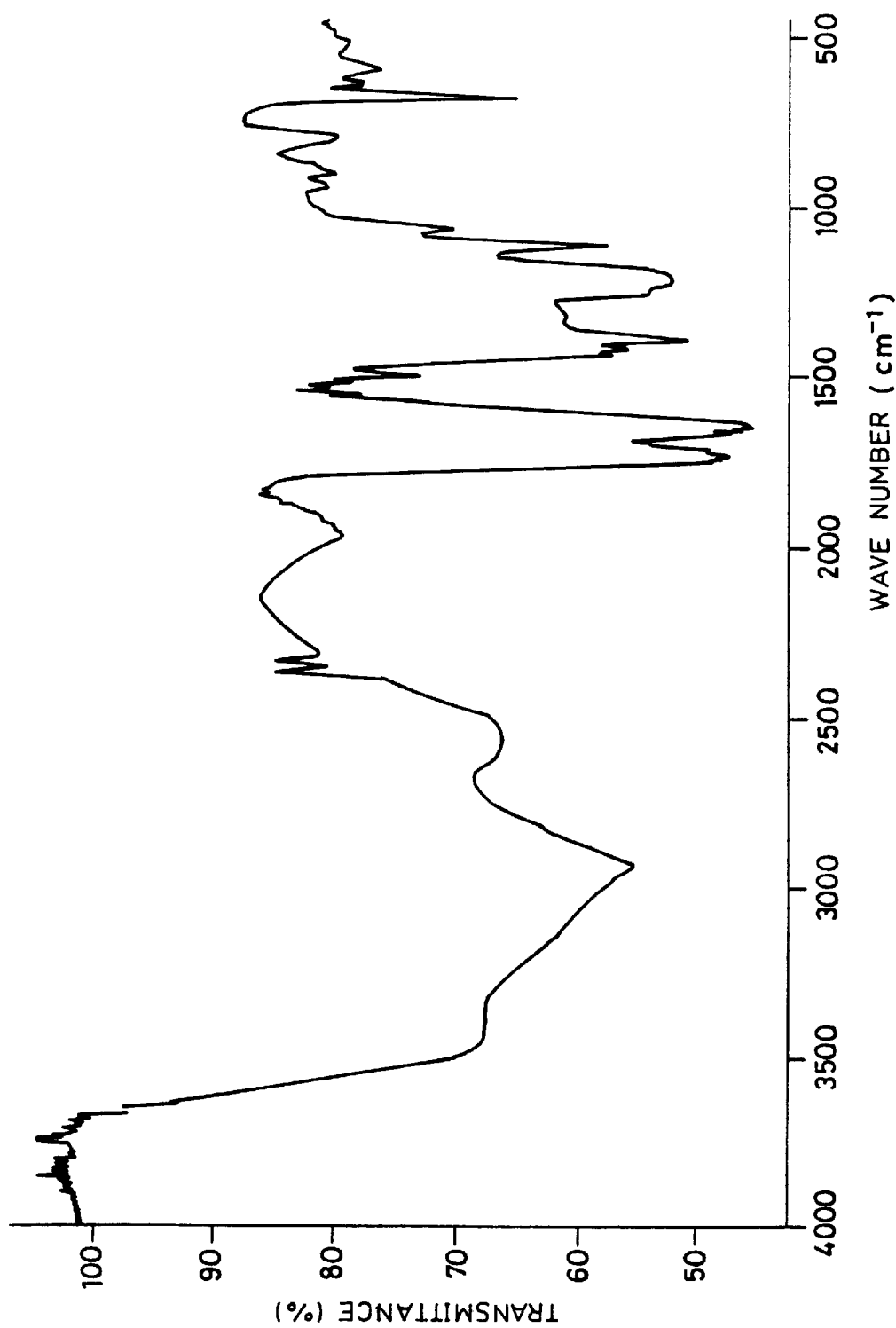
FIG. 7 shows an infrared absorption spectrum of a reaction product obtained in Example 4 of the present invention.
Figure 8:
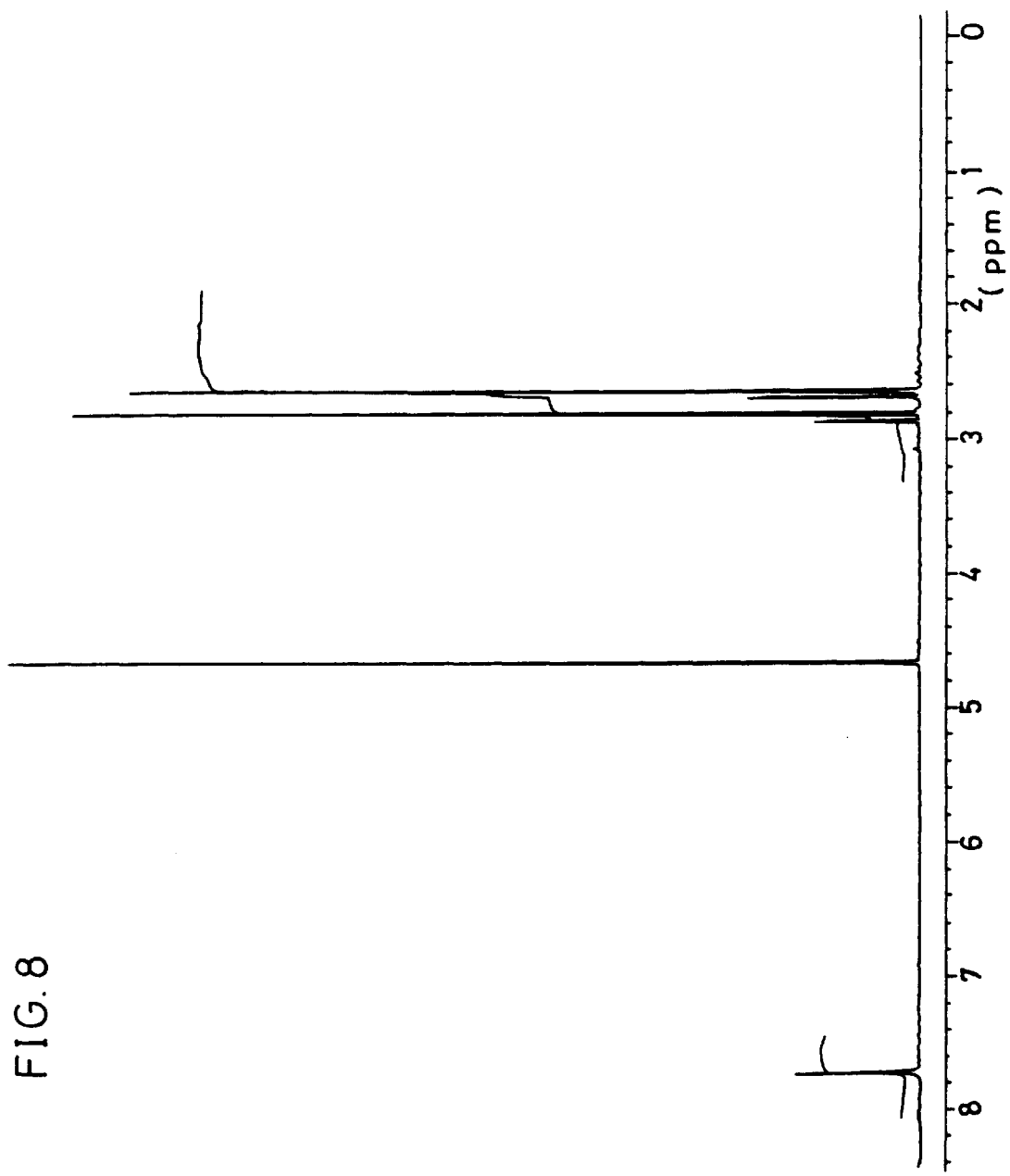
FIG. 8 shows a $^1$H-NMR chart of the reaction product of FIG. 7.

The resulting reactant product is identified, in the same manner as Example 1, to be a new monomer of the present invention. Also, it is acknowledged that the monomer is soluble to water. The infrared absorption spectrum and $^1$H-NMR of the resulting monomer are set forth in FIGS. 7 and 8, respectively.

(EXAMPLE 5)

To begin with, 490.3 parts of maleic anhydride (196 parts of the same is used as ethylenic unsaturated carboxylic acid serving as a raw material of a monomer, while 294.3 parts is used as ethylenic unsaturated carboxylic acid serving as a copolymer), 420 parts of citric acid monohydrate (poly carboxylic acid containing a hydroxyl group as a raw material of the monomer), 3 parts of p-toluenesulfonic acid (catalyst), and 0.01 part of ferrous ammonium sulfate hexahydrate (metal compound) are stirred in a four-neck 1 l -flask equipped with a thermometer, a stirring instrument and a reflux condenser, and the reactant solution is heated to 120° C. and let stand for 30 minutes at 120° C.

Next, the reactant solution is cooled to 80° C. and 93.75 parts of 48 wt % sodium hydroxide water solution serving as a basic compound and 406.3 parts of pure water serving as an aqueous medium are added. Then, the resulting water solution is subject to heating up to a boiling temperature with stirring under a normal pressure. As a result, a monomer, namely, maleic acid-citric acid ester (monoester), is prepared.

Next, 257.2 parts of 35 wt % aqueous hydrogen peroxide serving as a polymerization initiator is dropped to the above solution in 180 minutes. At the same time, 2,350 parts of 30 wt % sodium acrylate water solution serving as the ethylenic unsaturated monomer is dropped to the above solution in 140 minutes to let the monomer undergo polymerization. Note that a mole ratio among the monomer, maleic anhydride, and sodium acrylate is 24:16:60. The amount (mole ratio) of each compound used herein is set forth in TABLE 1 below.

When the reaction ends, 209.2 parts of 48 wt % sodium hydroxide water solution is added to the above solution to neutralize the same. As a result, a solution containing 38 wt % of solid content is obtained. The resulting solution is analyzed in a predetermined manner, and it is acknowledged that the solution includes a new polymer of the present invention.

The weight average molecular weight (Mw) of the polymer thus obtained (hereinafter, referred to as the polymer ①) and an amount (wt %) of a non-reacted monomer are evaluated by the gel permeation chromatography. In the evaluation, Asahi Chemical Asahi Pack GFA-7MF (Asahi Chemical Industry Co., Ltd.) is used as a column and 0.5 wt % phosphoric acid water solution is used as an eluent solution. Also, a sodium standard sample (Souwa Kagaku K.K.) is used as a molecular weight standard sample. The weight average molecular weight of the polymer ① is evaluated as 13,000 and a non-reacted monomer is evaluated as 0.4 wt %.

In addition, the biodegradability (%) of the polymer ① is computed by the biodegradability test explained below. Further, to check the physical properties of the polymer ① including chleating ability, calcium ion capturing ability ($mgCaCO_3/g$), a calcium ion stability constant, iron ion capturing ability, and clay dispersing ability are evaluated under the following conditions.

(a) Biodegradability Test

The biodegradability test is performed in accordance with the revised MITI (Ministry of International Trade and Industry) test based on Chemical Examination Law (regulations related to examination and production of chemical compounds).

To being with, a culture medium is prepared in a manner as follows. Liquids A, B, C, and D, which are specified in an article related to biochemical oxygen demand in JIS K 0102 (industrial waste water testing method), are prepared. To be more specific, liquid A is prepared by dissolving 21.75 g of potassium dihydrogenphosphate, 8.5 g of potassium monohydrogenphosphate, 44.6 g of sodium dihydrogenphosphate dodecahydride, and 1.7 g of ammonium chloride into 1 l of water. Liquid B is prepared by dissolving 22.5 g of magnesium sulfate heptahydride into 1 l of water. Liquid C is prepared by dissolving 27.5 g of calcium chloride anhydride into 1 l of water. Liquid D is prepared by dissolving 0.25 g of iron (III) chloride hexahydride into 1 l of water. A basic culture medium is prepared by adding 3 ml of each of Liquids A through D in alphabetical order to 1 l of distilled water.

Next, predetermined amounts of the basic culture medium thus prepared and the polymer ① serving as a test material are placed in a 500 ml-flask, and a pH of the resulting mixed solution is adjusted to 7 using sodium hydroxide. Then, TOC (Total Organic Carbon) of the mixed solution is evaluated. Next, a predetermined amount of pure water culture sludge (6,000 ppm) serving as an organism is placed into the flask. As a result, 300 ml of a test solution is prepared, in which the concentrations of the polymer ① and sludge are adjusted to 100 ppm and 30 ppm, respectively.

Also, a predetermined amount of the basic culture medium is placed into a 500 ml-flask and a pH of the same is adjusted to 7 using sodium hydroxide. As a result, 300 ml of a blank test solution containing no test material is prepared and TOC of the same is evaluated.

Then, both the flasks are capped with cotton and placed in a shaking type bioreactor with a constant temperature of 25°±3° C. Both the test solution and blank solution are cultured for 28 days while being rotated at 150 times/min to be shaken.

Immediately after the culturing, the supernatant of the test solution is subject to centrifugation at 3,000 rpm for 10 minutes using a centrigual separator to deposit the sludge and obtain supernatant. The TOC of the supernatant is evaluated and the TOC of the blank test solution is also evaluated.

The biodegradability ratio (%) of the polymer ① is computed as to be 25% using an equation:

$$\text{biodegradability ratio } (\%)=[\{(S_0-B_0)-(S_t-B_t)\}/(S_0 B_0)]\times 100$$

where $S_0$ is experimental data (mg/l) of the test solution before the culturing, $B_0$ is experimental data (mg/l) of the blank test solution before the culturing, $S_t$ is experimental data (mg/l) of the test solution after the culturing, and $B_t$ is experimental data (mg/l) of the blank test solution after the culturing.

(b) Calcium Ion Capturing Ability

The calcium ion capturing ability is evaluated in the following manner. To begin with, a calcium carbonate water solution having a calcium ion ($Ca^{2+}$) concentration of $1.0\times 10^{-3}$ mol/l is prepared by dissolving calcium carbonate ($CaCO_3$) into water. Then, 10 mg (conversion in solid content) of the polymer ① is placed into a 100 ml-beaker, and 50 ml of the above-prepared calcium carbonate water solution is added. The resulting sampling solution is stirred for 10 minutes at 25° C. using a magnetic stirrer.

After the stirring, a concentration of calcium ions of the sampling solution is evaluated using an ion analyzer (EA920 of Orion Co.) equipped with a calcium electrode (93-20 of Orion Co.). A concentration of calcium ions of the pre-stirring sampling solution is evaluated in the same manner in advance. Thus, a balance of the concentrations of calcium ions before and after the stirring is computed.

An amount of calcium ions captured by 1 g of the polymer ① is computed using the balance value (mol/l), which is converted into an amount of calcium carbonate ($mgCaCO_3/g$) and defined as the calcium ion capturing ability. The calcium ion capturing ability of the polymer ① is evaluated as 480 $mgCaCO_3/g$.

(c) Calcium Ion Stability Constant

The calcium ion stability constant is evaluated in the following manner. To begin with, three kinds of calcium chloride water solutions having concentrations of 0.002 mol/l, 0.003mol/l, and 0.004mol/l by dissolving calcium chloride ($CaCl_2$) into water.

Next, 50 g of the above-prepared water solutions are placed into three 100 ml-beakers, respectively. Then, 50 mg (conversion in solid content) of the polymer ① is added to each kind of water solution, and a pH of each sampling solution is adjusted to 10. Then, 0.15 g of sodium chloride (NaCl) serving as a calcium ion electrode stabilizer is added to each sampling solution, and a concentration of free calcium ions in the same is evaluated using the calcium electrode.

Let a concentration of free calcium ions be [Ca], a concentration of calcium ions fixed by the polymer ① be [CaS], the number of all the chelating sites of the polymer ① be $[S_0]$, the number of free chelating sites of the polymer ① be $[S]$, and the calcium ion stability constant be logK, then, $$[Ca]\cdot[S]/[CaS]=1/K$$

$$[S]=[S_0]-[CaS],$$

thus, $$[Ca]/[CaS]=(1/[S_0])\cdot[Ca]+1/([S_0]\cdot K).$$

Therefore, $[S_0]$ and K are computed easily using a slope and intercepts of a plot taking $[Ca]/[CaS]$ on ordinate and $[Ca]$ on abscissa. That is to say, the calcium ion stability constant logK can be computed easily.

The calcium ion stability constant of the polymer ① is computed as 6.2 using the evaluated concentration of free calcium ions.

(d) Iron Ion Capturing Ability

The iron ion capturing ability is evaluated in the following manner. To begin with, 0.1 wt % ferric chloride hexahydride water solution is prepared by dissolving ferric chloride hexahydride into water. Also, 0.1 wt % sodium hydroxide water solution is prepared by dissolving sodium hydroxide into water. Further, a 0.1 wt % water solution of the polymer ① (conversion in solid content) is prepared by dissolving the polymer ① into water. Next, 150 ml of the above-prepared ferric chloride water solution, 150 ml of the above-prepared sodium hydroxide solution, and 150 ml of the above-prepared polymer ① solution are mixed in a 500 ml-beaker to prepare a test solution. The resulting test solution is stirred for 5 minutes using a magnetic stirrer and let stand for 2 hours.

Next, the test solution is filtered using a 5 C filter paper and the filter paper is dried. The dried filter paper is pressed by a weight with a black back surface and covered with a black box, and an L value of the filter paper is evaluated using an SZ optical sensor (color measuring system) of Nihon Dennsyoku Ltd., Co.

Also a blank test solution is prepared by mixing 150 ml of the above-prepared ferric chloride water solution, 150 ml of sodium hydroxide water solution, and 150 ml of pure water in a 500 ml-beaker. An L value of the blank test solution thus prepared is also evaluated in the same manner as above.

The iron ion capturing ability is computed using the two L values and a following equation:

$$\text{iron ion capturing ability} = \left(\begin{array}{c} L \text{ value of} \\ \text{test solution} \end{array}\right) - \left(\begin{array}{c} L \text{ value of} \\ \text{blank solution} \end{array}\right).$$

The iron ion capturing ability of the polymer ① is evaluated as 14.0.

(e) Clay dispersing Ability

The clay dispersing ability is evaluated in the following manner. To begin with, 0.5 wt % water solution of the polymer ① (conversion in solid content) is prepared by dissolving the polymer ① into water. Then, 1 ml of the above-prepared polymer ① water solution and 100 g of tap water of Himeji-city, Hyogo, Japan are mixed in a 100 ml-measuring cylinder, and 1.0 g of amazon clay (clay) is added. The resulting sampling solution is stirred for 10 minutes using a magnetic stirrer and let stand for 18 hours.

Next, 10 ml of supernatant of the sampling solution is collected and absorbance (turbidity) of UV rays having a wave length of 380 nm is evaluated using a 1 cm-cell. The value thus evaluated is defined as the clay dispersing ability and the clay dispersing ability of the polymer ① is evaluated 1.5.

The weight average molecular weight, amount of non-reacted monomer, biodegradability, calcium ion capturing ability, calcium ion stability constant, iron ion capturing ability, and clay dispersing ability of the polymer ① are set forth in TABLE 2 below.

(EXAMPLES 6–12)

The reaction and operation are carried out in the same manner as Example 5 except that the kinds and/or amounts (mole ratio) of poly carboxylic acid containing a hydroxyl group or the ethylenic unsaturated monomer are changed as are set forth in TABLE 1 below, and polymers (hereinafter, respectively referred to as polymers ②–⑧) are obtained. The polymers ②–⑧ are evaluated in the same manner as Example 5, and the result of which are set forth in TABLE 2 below.

(EXAMPLE 13)

Here, 500 parts of toluene serving as a solvent, 172 parts of methyl acrylate serving as ethylenic unsaturated carboxylic acid, 420 parts of citric acid monohydrate, 3 parts of p-toluenesulfonic acid, 0.035 part of hydroquinone serving as a polymerization inhibitor are stirred in a four-neck 1 l-flask equipped with a thermometer, a stirring instrument and a reflux condenser at 100° C. for 3 hours, while distilling away a by-product, methanol.

Next, the reactant solution is heated under a reduced pressure to distill away toluene. Then, 0.01 part of ferrous ammonium sulfate hexahydrate, 93.75 parts of 48 wt % sodium hydroxide, and 406.3 parts of pure water are added, and the resulting solution is heated up to a boiling temperature with stirring under a normal pressure. As a result, a monomer, namely, acrylic acid-citric acid half ester, is prepared.

Then, 257.2 parts of 35 wt % aqueous hydrogen peroxide serving as a polymerization initiator and 100 parts of 15 wt % sodium persulfate water solution are dropped to the above solution in 180 minutes. At the same time, 2,506 parts of 30 wt % sodium acrylate water solution is dropped to the above solution in 180 minutes. As a result, the monomer undergoes polymerization. Note that a mole ratio between the monomer and sodium acrylate is 20:80. The amount (mole ratio) of each compound used herein is set forth in TABLE 1 below.

When the reaction ends, 209.2 parts of 48 wt % sodium hydroxide water solution is added to the above solution to neutralize the same. As a result, a solution containing 36 wt % of solid content is produced. It is acknowledged that the solution includes a new polymer of the present invention.

The polymer thus obtained (hereinafter, referred to as the polymer ⑨) is evaluated in the same manner as Example 5, and the result of which is set forth in TABLE 2 below.

(Comparative Example 1)

An evaluation is carried out in the same manner as Example 5 using a known compound, sodium polyacrylate having a weight average molecular weight of 2,200, and the result of which is set forth in TABLE 2 below.

(Comparative Example 2)

An evaluation is carried out in the same manner as Example 5 using a known compound, sodium citrate having a weight average molecular weight of 2,500, and the result of which is set forth in TABLE 2 below.

(Comparative Example 3)

An evaluation is carried out in the same manner as Example 5 using a known compound, sodium polymaleate having a weight average molecular weight of 800, and the result of which is set forth in TABLE 2 below.

(EXAMPLE 14)

Compositions of the present invention are produced out of the polymers ①–⑨, respectively. To be more specific, detergent compositions are produced as a composition containing 20 wt % (conversion in solid content) of each of the above polymers. Ingredients contained in the detergent composition and amounts (wt %) thereof are set forth in TABLE 3 below.

TABLE 1

| EXAMPLE | ETHYLENIC UNSATURATED CARBOXYLIC ACID (PARTS) | POLY CARBOXYLIC ACID CONTAINING HYDROXYL GROUP (PARTS) | MONOMER (a) HE: HALF ESTER | ETHYLENIC UNSATURATED MONOMER (PARTS) (b) W.S: WATER SOLUTION | | (a)/(b) MOLE RATIO |
|---|---|---|---|---|---|---|
| 5 | MALEIC ACID 196 | CITRIC ACID MONOHYDRATE 420 | MALEIC ACID-CITRIC ACID HE | 30 WT % SODIUM ACRYLATE W.S MALEIC ANHYDRIDE | 2,350 294.3 | 24/76 |
| 6 | MALEIC ACID 196 | CITRIC ACID MONOHYDRATE 420 | MALEIC ACID-CITRIC ACID HE | — | | 100/0 |
| 7 | MALEIC ACID 196 | CITRIC ACID MONOHYDRATE 420 | MALEIC ACID-CITRIC ACID HE | 30 WT % SODIUM ACRYLATE W.S MALEIC ANHYDRIDE | 6,000 294.3 | 8.3/91.7 |
| 8 | MALEIC ACID 196 | CITRIC ACID MONOHYDRATE 420 | MALEIC ACID-CITRIC ACID HE | 30 WT % SODIUM METHACRYLATE W.S MALEIC ANHYDRIDE | 2,700 294.3 | 24/76 |
| 9 | MALEIC ACID 196 | CITRIC ACID MONOHYDRATE 420 | MALEIC ACID-CITRIC ACID HE | 30 WT % SODIUM 3-ALLOXY-2-HYDROXYPROPANE SULFONATE W.S. MALEIC ANHYDRIDE | 5,450 294.3 | 24/76 |
| 10 | MALEIC ACID 196 | CITRIC ACID MONOHYDRATE 420 | MALEIC ACID-CITRIC ACID HE | ISOPRENOL MALEIC ANHYDRIDE | 645 294.3 | 24/76 |
| 11 | MALEIC ACID 196 | MALIC ACID 268 | MALEIC ACID-MALIC ACID HE | 30 WT % SODIUM ACRYLATE W.S MALEIC ANHYDRIDE | 2,350 294.3 | 24/76 |
| 12 | MALEIC ACID 196 | TARTARIC ACID 300 | MALEIC ACID-TARTARIC ACID HE | 30 WT % SODIUM ACRYLATE W.S MALEIC ANHYDRIDE | 2,350 294.3 | 24/76 |
| 13 | METHYL ACRYLATE 172 | CITRIC ACID MONOHYDRATE 420 | MALEIC ACID-CITRIC ACID HE | 30 WT % SODIUM ACRYLATE W.S | 2,506 | 20/80 |

TABLE 2

| EXAMPLE | WEIGHT AVERAGE MOLECULAR WEIGHT (Mw) | AMOUNT OF NON-REACTED MONOMER (WT %) | BIO-DEGRADABILITY RATIO (%) | CALCIUM ION CAPTURING ABILITY (mgCaCO$_3$/g) | CALCIUM ION STABILITY CONSTANT | IRON ION CAPTURING ABILITY | CLAY DISPERSING AGENT |
|---|---|---|---|---|---|---|---|
| 5 | 13,000 | 0.4 | 25 | 480 | 6.2 | 14.0 | 1.5 |
| 6 | 12,000 | 0.1 | 65 | 250 | 5.0 | 10.5 | 1.6 |
| 7 | 11,000 | 0.3 | 27 | 330 | 5.0 | 13.3 | 1.3 |
| 8 | 8,500 | 0.2 | 25 | 470 | 6.0 | 13.8 | 1.4 |
| 9 | 14,000 | 0.4 | 45 | 350 | 4.8 | 12.1 | 1.5 |
| 10 | 5,000 | 0.3 | 48 | 340 | 4.6 | 11.9 | 1.6 |
| 11 | 9,000 | 0.4 | 45 | 400 | 5.7 | 13.5 | 1.7 |
| 12 | 13,000 | 0.3 | 38 | 410 | 5.5 | 13.8 | 1.6 |
| 13 | 12,000 | 0.2 | 37 | 470 | 6.0 | 13.4 | 1.5 |
| *1 | 2,200 | — | 0.5 | 230 | 3.5 | 4.8 | 1.3 |
| *2 | 2,500 | — | 83 | 220 | 3.2 | 4.2 | 0.2 |
| *3 | 800 | — | 0.3 | 230 | 3.5 | 5.8 | 0.8 |

*COMPARATIVE EXAMPLE

TABLE 3

DETERGENT COMPOSITION

| INGREDIENTS | AMOUNT (WT %) |
|---|---|
| ONE OF THE POLYMERS ①–⑨ | 20 |
| STRAIGHT CHAIN SODIUM ALKYLBENZENE SULFONATE (HAVING 11.5 CARBON ATOMS IN AVERAGE) | 20 |
| ZEOLITE | 20 |
| POLYOXYETHYLENEALKYL ETHER (HAVING 12 CARBON ATOMS IN AVERAGE AT ALKYL PORTION) (HAVING CYCLING NUMBER OF 8 IN AVERAGE AT OXYETHYLENE PORTION) | 15 |
| SODIUM CARBONATE | 15 |
| No. 1 SODIUM SILICATE | 9.5 |
| ENZYME (PROTEASE) | 0.5 |

Also, to evaluate the performance of the above detergent compositions, sludge is produced artificially. Ingredients contained in the artificial sludge and amounts thereof are set forth in TABLE 4 below.

TABLE 4

ARTIFICIAL SCALE

| INGREDIENTS | AMOUNT(WT %) |
|---|---|
| CLAY | 49.75 |
| MYRISTIC ACID | 8.3 |
| OLEIC ACID | 8.3 |
| TRISTEARIC ACID | 8.3 |
| TRIOLEIN | 8.3 |
| CHOLESTEROL | 4.38 |
| CHOLESTERIN STEARATE | 1.09 |
| PARAFFIN WAX (MELTING POINT 50° C.–52° C.) | 0.552 |
| SQUALENE | 0.552 |
| CARBON BLACK (DESIGNATED BY OILCHEMICAL ASSOCIATION) | 0.5 |
| MOISTURE | 9.976 |

A detergent test is performed using the above artificial sludge. To begin with, the artificial sludge is dispersed in carbon tetrachloride, and a white cotton cloth is soaked in the resulting dispersed solution. Then, the cloth is dried, cut into a square piece of 10 cm×10 cm, and washed under the conditions set forth in TABLE 5 below.

TABLE 5

WASHING CONDITIONS

| | |
|---|---|
| TEMPERATURE | 20° C. |
| BATH RATIO | 1/60 |
| CONCENTRATION OF DETERGENT COMPOSITION | 0.3 WT % |
| WATER QUALITY | TAP WATER |
| TERG-O-TOMETER (UESHIMA SEISAKUSHO CO., LTD) | 10 MINS. |

When the cleaned cloth is dried, the reflectance of the same is evaluated in a predetermined manner, and the detergentcy rate is computed by:

detergency rate (%) = (reflectance of the washed cloth – reflectance of the dirty cloth before washing)/(reflectance of a white cloth – reflectance of the dirty cloth before washing) × 100.

The evaluation result is set forth in TABLE 6 below.

(Comparative Example 4)

The detergent test is carried out in the same manner as Example 14 using a compound used in Comparative Example 1, that is, sodium polyacrylate, as the detergent composition and the detergency rate is computed. The evaluation result is set forth in TABLE 6 below.

(Comparative Example 5)

The detergent test is carried out in the same manner as Example 14 using a compound used in Comparative Example 2, that is, sodium citrate, as the detergent composition, and the detergency rate is computed. The evaluation result is set forth in TABLE 6 below.

(Comparative Example 6)

The detergent test is carried out in the same manner as Example 14 using a compound used in Comparative Example 3, that is, sodium polymaleate, as the detergent composition and the detergency rate is computed. The evaluation result is set forth in TABLE 6 below.

TABLE 6

| POLYMER INCLUDED IN DETERGENT COMPOSITION | DETERGENCY RATE (%) |
|---|---|
| POLYMER ① | 98 |
| POLYMER ② | 96 |
| POLYMER ③ | 96 |
| POLYMER ④ | 97 |
| POLYMER ⑤ | 96 |
| POLYMER ⑥ | 96 |
| POLYMER ⑦ | 98 |
| POLYMER ⑧ | 98 |
| POLYMER ⑨ | 98 |
| COMPARATIVE EXAMPLE 4 | 82 |
| COMPARATIVE EXAMPLE 5 | 80 |
| COMPARATIVE EXAMPLE 6 | 82 |

TABLE 6 reveals that the detergent compositions including the polymers ①–⑨ of the present invention renders higher detergency compared with those including the known compounds.

(EXAMPLE 15)

Compositions of the present invention are produced out of the polymers ①–⑨. To be more specific, fiber treatment agents respectively containing 2 g/l (conversion in solid content) of the polymers ①–⑨ are produced. Ingredients contained in the fiber treatment agents and amounts thereof are specified below. Note that the fiber treatment agents referred herein are water solutions.

| (Ingredients) | |
|---|---|
| One of the polymers ①–⑨ | 2 g/l |
| Hydrogen peroxide | 10 g/l |
| Sodium hydroxide | 2 g/l |
| No. 3 Sodium silicate | 5 g/l |

Bleaching tests are carried out using the above fiber treatment agents and a cotton grey sheeting knit cloth. The bleaching conditions are specified below.

| (Bleaching conditions) | |
|---|---|
| Hardness of water | 35 · DH (German Hardness) |
| Bath ratio | 1:25 |
| Temperature | 85° C. |
| Time | 20 mins. |

The feeling of the bleached cloth is checked by the functional inspection method.

Also, the whiteness (W value) of the same is evaluated by a whiteness equation based on Lab below using parameters evaluated using a 3M color computer SM-3 model of Suga Shiken Kiki K.K:

$$W=100-[(100-L)^2+a^2+b^2]^{1/2}$$

where L is a evaluated lightness a is an evaluated chromaticness index of red, and b is an evaluated chromaticness index of blue.

Further, the readiness in sewing is evaluated by the number of thread breakages in the textile when an idle #11S thread of a sewing machine is run on a 4-layer cloth for 30 cm. The result of evaluation is set forth in TABLE 7 below.

(Comparative Examples 7–9)

The bleaching tests are carried out in the same manner as Example 15 using the compounds of Comparative Examples 4–6 in numerical order as the fiber treatment agents. The feeling of each bleached cloth is checked, and the whiteness and the number of thread breakages in the textile are evaluated, and the results of which are set forth in TABLE 7 below.

TABLE 7

| POLYMER INCLUDED IN FIBER TREATMENT AGENT | FEELING | WHITENESS (W VALUE) | READINESS IN SEWING (Nos OF BREAKAGES) |
|---|---|---|---|
| POLYMER ① | ○ | 98 | 36 |
| POLYMER ② | ○ | 94 | 37 |
| POLYMER ③ | ○ | 98 | 34 |
| POLYMER ④ | ○ | 97 | 37 |
| POLYMER ⑤ | ○ | 95 | 38 |
| POLYMER ⑥ | ○ | 95 | 36 |
| POLYMER ⑦ | ○ | 96 | 30 |
| POLYMER ⑧ | ○ | 96 | 35 |
| POLYMER ⑨ | ○ | 98 | 38 |
| COMPARATIVE EXAMPLE 7 | Δ | 86 | 70 |
| COMPARATIVE EXAMPLE 8 | X | 86 | 79 |
| COMPARATIVE EXAMPLE 9 | Δ | 88 | 69 |

○: SOFT
Δ: RATHER HARD
X: FAIRLY HARD

TABLE 7 reveals that the fiber treatment agents using the polymers ①–⑨ of the present invention excel those using the known compounds in feeling and whiteness, and considerably reduce the number of the thread breakages in the textile.

(EXAMPLE 16)

Compositions of the present invention are produced out of the polymers ①–⑨. To be more specific, dispersing solutions are prepared by using the polymers ①–⑨ as inorganic pigment dispersing agents in the following manner.

To begin with, calcite-based cubic soft calcium carbonate (primary particle diameter: 0.15 μm) is dehydrated by the filter pressing, and 400 parts of a resulting cake (solid content: 65.3 wt %) is placed in a 1 l-beaker (material: SUS304, inner diameter: 90 mm, height: 160 mm). Then, 3.26 parts of a 40 wt % polymer water solution serving as an inorganic pigment dispersing agent (a ratio of the polymer to calcium carbonate is 0.5 wt %) is poured into the beaker, and 6.9 parts of water is added to adjust the concentration of the solid content. Then, the reactant is kneaded slowly for 3 minutes using a dissolver stirring blade (50 mmφ), and subject to dispersion for 10 minutes at 3,000 rpm. As a result, a dispersing solution whose concentration of solid content is 64 wt % is obtained.

The viscosity (cP) of the resulting dispersing solution immediately after the dispersion, and the viscosity (cP) after having let the same stand for a week at room temperature are evaluated at 25° C. using a B-type viscometer. The result of evaluation is set forth in TABLE 8 below.

(Comparative Examples 10–12)

Dispersing solutions are prepared in the same manner as Example 16 using the compounds of Comparative Examples 4–6 in numerical order as the inorganic pigment dispersing agent. The viscosity of each dispersing solution is evaluated, and the result of which is set forth in TABLE 8 below.

TABLE 8

| | VISCOSITY OF DISPERSING SOLUTION (cP) | |
|---|---|---|
| POLYMER INCLUDED IN INORGANIC PIGMENT DISPERSING AGENT | IMMEDIATELY AFTER | AFTER A WEEK |
| POLYMER ① | 330 | 380 |
| POLYMER ② | 320 | 370 |
| POLYMER ③ | 350 | 360 |
| POLYMER ④ | 340 | 370 |
| POLYMER ⑤ | 350 | 380 |
| POLYMER ⑥ | 390 | 430 |
| POLYMER ⑦ | 390 | 410 |
| POLYMER ⑧ | 420 | 450 |
| POLYMER ⑨ | 410 | 430 |
| COMPARATIVE EXAMPLE 10 | 600 | 800 |
| COMPARATIVE EXAMPLE 11 | 10,000 | — |
| COMPARATIVE EXAMPLE 12 | 3,000 | — |

TABLE 8 reveals that the dispersing solutions using the polymers ①–⑨ of the present invention renders higher dispersing ability and maintains the same satisfactorily after having been let stand for a week compared with those using the known compounds.

(EXAMPLE 17)

Compositions of the present invention are produced out of the polymers ①–⑨, respectively. To be more specific, the polymers ①–⑨ are used as bleaching assistant for wood pulp (pre-treatment agent) to bleach the wood pulps in the following manner.

To begin with, 30 parts (absolute dry weight) of gland pulps is placed in a 5l-beaker, and 3,000 parts of water of 50° C. and 0.06 part of a polymer serving as a bleaching assistant are added (a ratio of the polymer to the pulp is 0.2 wt %). Then, the reactant is stirred for 15 minutes at 50° C. Next, the pulp is separated from the treated solution through filtration using a so-called No. 2 filter paper, and the removed pulp is washed with 1,500 parts of water and dehydrated.

Next, the pulp obtained by the above pre-treatment is placed in a 5 l-beaker, and water is added until the concentration of the pulp in the solution is adjusted to 14 wt %. Also, a pH of the resulting treated solution is adjusted to 11.0 by adding hydrogen peroxide (a ratio of the same to the pulp is 4 wt %), No. 3 sodium silicate, and sodium hydroxide.

The resulting treated solution is placed in a polyethylene bag, and the opening of the bag is folded to prevent the moisture evaporation. Then, the bag is placed in a water bath maintained at 65° C. and heated for 5 hours to bleach the pulp. The bleached pulp is filtered using a 420-mesh filter cloth and dehydrated. Then, the concentration of hydrogen peroxide remaining in the filtrate is evaluated, and a consumption rate of hydrogen peroxide is computed by:

$$\text{consumption rate of hydrogen peroxide (\%)} = [(B-C)/B] \times 100$$

where B is a concentration (wt %) of hydrogen peroxide in the treatment solution before the bleaching, and C is a concentration of hydrogen peroxide in the treatment solution after the bleaching.

A part of the bleached pulp is diluted to 3 wt % with water, and a pH is adjusted to 4.5 using aqueous sulfurous acid. As a result, a pulp slurry is produced. Then, two hand-made sheets are produced out of the pulp slurry by the standard method of the Technical Association of the Pulp and Paper Industry. When the sheets are air-dried, the whiteness by Hunter of the same is evaluated using the whiteness by Hunter checking instrument. The result of the evaluation is set forth in TABLE 9 below.

(Comparative Examples 13–15)

Wood pulps are bleached in the same manner as Example 17 using the compounds used in Comparative Examples 4–6 in numerical order as the bleaching assistants for wood pulp. The consumption rate and whiteness of each bleached pulp are evaluated, and the result of which is set forth in TABLE 9 below.

TABLE 9

| POLYMER INCLUDED IN INORGANIC PIGMENT DISPERSING AGENT | CONSUMPTION RATE OF HYDROGEN PEROXIDE (%) | WHITENESS BY HUNTER (%) |
|---|---|---|
| POLYMER ① | 70.5 | 81.5 |
| POLYMER ② | 71.2 | 80.7 |

TABLE 9-continued

| POLYMER INCLUDED IN INORGANIC PIGMENT DISPERSING AGENT | CONSUMPTION RATE OF HYDROGEN PEROXIDE (%) | WHITENESS BY HUNTER (%) |
|---|---|---|
| POLYMER ③ | 70.8 | 82.1 |
| POLYMER ④ | 71.4 | 80.6 |
| POLYMER ⑤ | 70.6 | 80.2 |
| POLYMER ⑥ | 72.1 | 79.7 |
| POLYMER ⑦ | 70.7 | 81.1 |
| POLYMER ⑧ | 70.8 | 81.2 |
| POLYMER ⑨ | 71.3 | 80.6 |
| COMPARATIVE EXAMPLE 13 | 77.3 | 75.9 |
| COMPARATIVE EXAMPLE 14 | 84.9 | 70.5 |
| COMPARATIVE EXAMPLE 15 | 79.8 | 75.3 |

TABLE 9 reveals that the bleaching assistants using the polymers ①–⑨ of the present invention excel those using the known compounds in whiteness, and consume less hydrogen peroxide. Thus, the bleaching assistants using the polymers ①–⑨ are economical because they demand less amount of hydrogen peroxide.

The invention being thus described, it will be obvious that the same may be varied in many ways. Such variations are not to be regarded as a departure from the spirit and scope of the invention, and all such modification as would be obvious to one skilled in the art are intended to be included within the scope of the following claims.

What is claimed is:

1. A monomer having a structure expressed as:

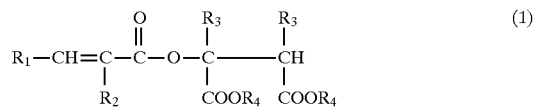

wherein $R_1$ is a hydrogen atom, $R_2$ is a hydrogen atom or a —$CH_3$ group, $R_3$ is a hydrogen atom, a —OH group, or a —$CH_2COOR_4$ group, and $R_4$ is a hydrogen atom, a sodium atom, a potassium atom, or a $NH_4$ group, provided that both groups $R_3$ cannot be a hydrogen atom at the same time and when the substituent group $R_2$ is a —$CH_3$ group, neither of groups $R_3$ is a hydrogen atom.

* * * * *